United States Patent
Conradsen et al.

(10) Patent No.: US 10,238,330 B2
(45) Date of Patent: Mar. 26, 2019

(54) METHOD OF INDICATING THE PROBABILITY OF PSYCHOGENIC NON-EPILEPTIC SEIZURES

(71) Applicant: Brain Sentinel, Inc., San Antonio, TX (US)

(72) Inventors: Isa Conradsen, København S (DK); Kim Gomme Gommesen, Odense N (DK)

(73) Assignee: Brain Sentinel, Inc., San Antonio, TX (US)

( * ) Notice: Subject to any disclaimer, the term of this patent is extended or adjusted under 35 U.S.C. 154(b) by 504 days.

(21) Appl. No.: 14/900,283

(22) PCT Filed: Jun. 20, 2014

(86) PCT No.: PCT/DK2014/050182
§ 371 (c)(1),
(2) Date: Dec. 21, 2015

(87) PCT Pub. No.: WO2014/202098
PCT Pub. Date: Dec. 24, 2014

(65) Prior Publication Data
US 2016/0296156 A1    Oct. 13, 2016

(30) Foreign Application Priority Data
Jun. 21, 2013    (DK) .................... 2013 70337

(51) Int. Cl.
*A61B 5/00* (2006.01)
*A61B 5/11* (2006.01)
(Continued)

(52) U.S. Cl.
CPC .......... *A61B 5/4094* (2013.01); *A61B 5/0488* (2013.01); *A61B 5/11* (2013.01);
(Continued)

(58) Field of Classification Search
CPC ........ A61B 5/4094; A61B 5/4088; A61B 5/11
See application file for complete search history.

(56) References Cited

U.S. PATENT DOCUMENTS 8,738,121 B2    5/2014 Virag et al.
8,805,484 B2    8/2014 Syed et al.
(Continued)

FOREIGN PATENT DOCUMENTS

WO    2007/034476 A2    3/2007
WO    2009/020880 A1    2/2009
WO    2013/010543 A1    1/2013

OTHER PUBLICATIONS

Barbara Mostacci, Francesca Bisulli, Lara Alvisi, Laura Licchetta, Agostino Baruzzi, Paolo Tinuper, Ictal Characteristics of Psychogenic Nonepileptic Seizures: What We Have Learned From Video/EEG Recordinds—A Literature Review, Epilepsy & Behavior, Academic Press, San Diego, CA, US, vol. 22, No. 2, Jul. 5, 2011, pp. 144-153.

(Continued)

*Primary Examiner* — Sean P Dougherty
*Assistant Examiner* — Nicholas E Kolderman
(74) *Attorney, Agent, or Firm* — Pizarro Allen PC

(57) ABSTRACT

A method and system for detecting a probability of psychogenic non-epileptic seizures using a portable battery powered device placed on the body of a patient and a device for manually logging detected seizures within a time period. The device may, advantageously, have a seizure detection algorithm which automatically records seizures detected within that time period. The two sets of data may then be transferred to a another device where the logged time stamps are matched to the recorded time stamps for determining if the detected seizure is a generalized tonic-clonic seizure (GTCS) or might be a psychogenic nonepileptic seizure (PNES). This provides a cheap and simple method for (Continued)

registering a probability of PNES by using a seizure detection device having an EMG-sensor or an accelerometer.

14 Claims, 1 Drawing Sheet

(51) Int. Cl.
*A61B 5/0488* (2006.01)
*G06F 19/00* (2018.01)

(52) U.S. Cl.
CPC .......... *A61B 5/7275* (2013.01); *A61B 5/7282* (2013.01); *G06F 19/00* (2013.01); *A61B 5/0002* (2013.01); *A61B 5/0022* (2013.01); *A61B 5/6824* (2013.01); *A61B 2562/0219* (2013.01)

(56) References Cited

U.S. PATENT DOCUMENTS

| | | | |
|---|---|---|---|
| 2009/0171168 A1 | 7/2009 | Leyde et al. | |
| 2011/0166430 A1* | 7/2011 | Harris | A61B 5/0031 600/301 |
| 2012/0083700 A1* | 4/2012 | Osorio | A61B 5/0245 600/483 |
| 2012/0083701 A1* | 4/2012 | Osorio | A61B 5/4094 600/483 |
| 2012/0116183 A1* | 5/2012 | Osorio | A61B 5/4094 600/301 |
| 2012/0245481 A1* | 9/2012 | Blanco | A61B 5/048 600/544 |
| 2014/0163413 A1 | 6/2014 | Conradsen et al. | |

OTHER PUBLICATIONS

Fiona M. Cuthill, Colin A Espie, Sensitivity and Specificity of Procedures for the Differential Diagnosis of Epileptic and Non-Epileptic Seizures: A Systematic Review, Seizure, Bailliere Tindall, London, GB, vol. 14, No. 5, Jul. 1, 2005, p. 293-303.

Supplementary European Search Report for Application No. EP 14 81 4452, dated Jan. 11, 2017.

Ming-Zher Poh et al., Convulsive Seizure Detection Using a Wrist-Worn Electrodermal Activity and Accelerometry Biosensor, Harvard—MIT Division of Health Sciences and Technology, Massachusetts Institute of Technology, 75 Amherst St., Cambridge, MA 02139, USA; vol. 53, NR. 5, pp. e93-e97.

Isa Conradsen, et al., Evaluation of Novel Algorithm Embedded in a Wearable sEMG Device for Seizure Detection; DTU Electrical Engineering, KGS. Lyngby, 34th Annual International Conference of the IEEE EMBS San Diego, CA, USA, Aug. 1-Sep. 1, 2012, vol. 2012, p. 2048-2051.

Juliana Lockman, et al.; Detection of Seizure-Like Movements Using a Wrist Accelerometer; Epilepsy and Behavior, (2011), vol. 20, No. 4, p. 638-641.

Jade Bayly et al.; Time-Frequency Mapping of the Rhythmic Limb Movements Distinguishes Convulsive Epileptic From Psychogenic Nonepileptic Seizures; The Melbourne Brain Centre, The Royal Melbourne Hospital, Parkville, Victoria, Australia Article First Published Online May 3, 2013; vol. 54, NR. 8, p. 1402-1408.

T. Ryan Burchfield et al.; Accelerometer-Based Human Abnormal Movement Detection in Wireless Sensor Networks; UTDCS-19-07 and Poster in Healthnet '07; Proceedings of the 1st ACM SIGMOBILE International Workshop on Systems and Network Support for Healcare and Assisted Living Environments Located With International Conference on Mobile Systems.

Sandor Beniczky et al.; Detection of Generalized Tonic-Clonic Seizures by a Wireless Wrist Accelerometer: A Prospective, Multicenter Study; Epilepsia, vol. 54, No. 4, p. e58-e61, 2013.

Iiker H. Ipekdal et al.; Can Cortical Silent Period and Motor Threshold be Practical Parameters in the Comparison of Patients With Generalized Epilepsy and Patients With Psychogenic Non-Epileptic Seizures?; European Neurology 2013; 69 pp. 41-47.

Ian Rosemergy et al; Use of Postictal Respiratory Pattern to Discriminate Between Convulsive Psychogenic Nonepileptic Seizures and Generalized Tonic-Clonic Seizures; Epilepsy & Behavior,vol. 27, 2013, pp. 81-84.

\* cited by examiner

METHOD OF INDICATING THE PROBABILITY OF PSYCHOGENIC NON-EPILEPTIC SEIZURES

BACKGROUND OF THE INVENTION

Field of the Invention

The present invention relates to a method of indicating the probability of non-epileptic seizures, such as psychogenic non-epileptic seizures (PNES), wherein the method comprises the steps:
  automatically recording data on a patient by means of a first device placed on the body of the patient, wherein at least one sensor unit in the device measures at least one parameter on the body of the patient, and wherein the data is recorded over a predetermined time period;
  transmitting the data from the first device to a computer unit for further analysis; and
  manually logging data comprising at least a first time stamp of at least one seizure within that time period.

The present invention further relates to a system for indicating the probability of non-epileptic seizures, such as psychogenic non-epileptic seizures, comprising:
  a first device configured to be placed on the body of a patient, wherein the first device comprises at least one sensor unit configured to measure at least one parameter on the body of the patient, wherein the first device is configured to automatically record data over a predetermined time period;
  a computer unit configured to be coupled to the first device and comprising data processing means configured to analyze the recorded data; and
  means for manually logging data comprising at least a first time stamp of at least one seizure within that time period.

Description of Related Art

Today, seizures are a symptom for several diseases, which may make it hard for the doctors to diagnose the cause, especially due to the seizures resemblance with epileptic seizures. In particular psychogenic non-epileptic seizures (called PNES or NEAD) look very similar to epileptic seizures. This means that patients are often misdiagnosed, and resent studies have indicated that up to one-fourth of patients have been misdiagnosed. Correcting the diagnosis often involves a time-consuming and costly process. Especially, PNES similar to generalized tonic-clonic epileptic seizures (called GTCS) are hard to distinguish from actual GTCS without video and EEG (electroencephalography) recordings of the seizures.

Therefore, people suffering from PNES are often admitted to special clinics or hospitals where the medical staffs, such as physician, primary caregivers, doctors or neurologists, are able to monitor and record such seizures in order to determine the type of seizure and prepare a treatment. Once admitted, the patient is often coupled to an epilepsy monitoring unit (called an EMU) where seizures may be recorded on video combined with EEG-measurements. Such admissions in an EMU are very expensive and may cost as much as DKK 60,000 (about US$ 8,750), and requires the patient to be admitted for several hours or days in order to record a suitable amount of seizures. Provocative tests may be used by the staff to trigger seizures, if the seizures do not occur naturally during admission.

Today, video-EEG monitoring (called video-EEG) is the gold standard for detecting epilepsy and PNES. Both modalities are needed, and video monitoring alone does not provide an accurate way of detecting seizures. The EEG measurement involves the use a plurality of electrodes attached to the brain of the patient which are then coupled to a data logger or a data processing unit. Today, small portable EEG-devices may be coupled to the electrodes so that the patient is able to move around, but the multiple electrodes still provides some discomfort for the patient and increases the risk that one or more of the electrodes accidently fall off or are pulled off. Video-EEG is also used for verifying the accuracy (false detection rate) of seizure detection systems, however they still require the patient to be admitted and coupled to an EEG system.

The article "Can Cortical Silent period and Motor Threshold be Practical Parameters in the Comparison of Patients with Generalized Epilepsy and Patients with Psychogenic Non-Epileptic Seizures?", Ipekdal et al., Eur Neurol, 2013, discloses a method of distinguishing between a GTCS and a PNES where the patients were coupled to an EEG-device with a plurality of electrodes. The patients were admitted to a hospital and magnetically stimulated in the area controlling the ABP muscles of the brain by TMS. EMG electrodes placed on the ABP muscles are used to regulate the applied stimulate. The article teaches that cortical silent periods in the recorded EEG-signals are prolonged for patients with GTCS compared to patients with PNES. The article does not teach or suggest that the amplitude of the muscle activity may be used to detect PNES, since they found no significant differences in the recorded motor thresholds. This method requires patients to be admitted for at least two days which presents a time-consuming and costly process. The patients have to be subjected to a stimulant in the TSM test which may lead to some discomfort for the patient, as mentioned in the article.

The article "Use of postictal respiratory pattern to discriminate between convulsive psychogenic nonepileptic seizures and generalized tonic-clonic seizures", Rosemergy et al., Epilepsy Behav., April 2013, discloses a method of distinguishing between a GTCS and a PNES where the patients were admitted to a hospital and coupled to a video-monitoring unit. The postictal phase was then recorded at each seizure. This article teaches that the postictal respiratory response (rate and pattern) is significantly longer for patients with GTCS compared to patients with PNES. As mentioned in the article, the patient needs to be placed relative to the camera so that the respiratory response can be recorded, which is not always possible. The patient still needs to be admitted in order to get a proper video-recording of the patient.

The article "Detection of generalized tonic-clonic seizures by a wireless wrist accelerometer: A prospective, multicenter study", Beniczky et al., Epilepsia, April 2013, pg. 58-61, discloses a wristband comprising a three-axis accelerometer and a wireless Bluetooth module. A generic seizure detection algorithm for detecting a GTCS is implemented in the device and the recorded data is transmitted to a control unit which then generates an alarm. This article does not teach or suggest that the implemented algorithm and the recorded acceleration data may be used to detect a PNES or other non-epileptic seizures. Furthermore, the article does not teach or suggest how a GTCS may be distinguished from a PNES.

U.S. Patent Application Publication 2012/0116183 A1 discloses a device for automatically distinguishing between an epileptic and non-epileptic seizure by measuring two signals on a body and comparing the signals with two index classes respectively in order to determine a first and second index value. The index values are used to determine whether the sensed seizure is an epileptic or non-epileptic seizure.

Each seizure is automatically detected using a seizure detection algorithm, and a manual input from the patient or a caregiver is used to confirm whether the patient is having a seizure or not. This configuration provides a complex solution which requires a large amount of data processing as the classification process is performed each time a seizure is detected. The device is operated in an alarm mode informing the patient/caregiver of every detected seizure onset, thereby influencing the patient's assessment of when he/she is having a seizure.

International Patent Application Publication WO 2009/020880 A1 discloses a system for detecting epileptic seizures and PNES where the motor activity of the patient is continuously recorded using a sensor device and transferred to a computer unit that extracts features from the data stream using two dedicated analysis algorithms. Continuous video-EEG monitoring is used to determine when the seizures are occurring which are then used by the computer unit to define the time windows in which the data stream should be analyzed. The extracted features are then evaluated according to standard classification guidelines in order to determine whether the seizure is an epileptic seizure or a PNES. This solution requires the patient to be coupled to a conventional video-EEG monitoring system for logging seizures which in turn increases the cost for diagnosing a patient. The sensor device acts as a simple recording device, it is not able to detect when a seizure is occurring.

SUMMARY OF THE INVENTION

It is an object of the invention to provide a cheaper and simpler method of detecting psychogenic non-epileptic seizures.

It is an object of the invention to provide a method of detecting tonic-clonic seizures and psychogenic non-epileptic seizures which does not involve admitting the patient.

It is an object of the invention to provide the use of a portable seizure detection device to distinguish between tonic-clonic seizures and psychogenic non-epileptic seizures.

As mentioned above the invention relates to a method of indicating the probability of non-epileptic seizures, such as psychogenic non-epileptic seizures, characterised by:
  detecting at least one seizure within that time period using the device and recording at least a second time stamp of that seizure;
  comparing the recorded data to the logged data in the computer unit, and
  determining if the second time stamps match the first time stamps or not.

This provides a simple and cheap method of indicating the probability of PNES as well as GTCS in a patient. The present invention does not require the patient to be admitted to a hospital or a special clinic (e.g., an EMU) and coupled to an EEG system. Data may be automatically recorded by any small battery powered device configured to be placed on the body of the patient, e.g., on an arm, a leg or the torso. This allows the patient to be situated in his or hers normal environment thus providing a more accurate indication of the factors triggering the seizures. The patient may not act normally, if he or she was admitted thus providing a less accurate indication of the factors triggering the seizures. "Automatic recording" is defined as any device, either placed on the patient or coupled to a sensing unit placed on the patient, configured to store the sensed parameters without any human interaction, while "manually logging" is defined as any human interaction that requires the patient or subject to actively record or log the data either physically or electronically.

In one embodiment, the first device may continuously log or record data during the time period, e.g., up to seven days. The data may be stored in a memory unit in the first device or transmitted to a third device, such as a base unit, which then stores the data. The data file comprises at least a time stamp of each detected seizure. The size and weight of the device may be reduced, if the data is stored in the base unit. After the time period has lapsed, data may be transmitted to a second device, such as a central computer unit, via a wired or wireless connection. The data may instead be transferred to the second device via a temporary storage unit, such as a memory stick.

The patient may physically log the seizures by noting at least a time stamp on a list or electronically log the seizures, e.g., by activating a data logging device by means of a push of a button. The medical staff, such as physicians, primary caregivers, doctors, or neurologists, may then analyze the recorded data or time stamps from the first device and compare it to the logged data or time stamps from the patient.

The present invention is able to log seizures that are only registered by the device and not the patient, and vice versa. This configuration allows PNES to be distinguished from GTCS by comparing the two lists of time stamps with each other. If the first device has not recorded any seizures and the patient has logged one or more seizures, then the patient may suffer from PNES. If the first device has recorded one or more seizures and the patient has logged the same seizures, then the patient suffers from epileptic GTCS. If the patient has logged more seizures than those recorded by the device, then the patient may suffer from both PNES and epilepsy. In the event that the patient has not experienced any seizures, a new measuring time period may be performed. This provides an alternative method for distinguishing between PNES and GTCS that does not require the use of video-EEG to log seizures or a manual input to confirm the onset of a seizure.

In one embodiment, the two sets of data may be electrically compared in the second device. The second device may visually indicate each recorded or logged seizure and/or any matches or mismatches between the two sets of data. This allows for a simple and quick identification of each registered seizure and any mismatches between the two lists.

According to one embodiment, the first device compares the measured parameter to at least one threshold value and determines whether a seizure is present or not in a non-alarm mode.

The data may advantageously be recorded using any seizure detection devices comprising an algorithm for detecting GTCS or any seizures having a tonic and/or a clonic phase or any seizures having at least tonic activity. Detecting whether a seizure is present or not is defined as comparing the sensed and optionally filtered parameters to one or more sets of threshold values or reference patterns, and indicating by means of an event signal, such a high or low binary signal, whether these parameters fall within the intervals defined by the threshold values or patterns or not. The data recording may be activated when the device detects a seizure onset. Alternatively, the seizure detection algorithm may be implemented in the base unit instead. This allows the device, or the base unit, to record or log any seizure, such as any epileptic seizures, occurring within the time period. The amount of stored and processed data may be reduced by only recording data once a seizure has been detected. This allows the power consumption of the device to be reduced, thus increasing the operation time of the device.

In one embodiment, the seizure detection device may operate in a non-alarm mode, which defines a mode in which the device or the base unit does not activate or generate any audio and/or visual alarm or warning directing the patient's attention to an occurring seizure. This allows the manual data logging not to be influenced by the automatic data logging, thereby ensuring that the patient only logs data when he or she believes that a seizure has occurred. This is different from the device of U.S. patent application publication 2012/0116183 A1, which describes an alarm mode in which it informs the patient once a seizure is detected and allows the patient to confirm or disconfirm that he/she is having a seizure. The non-alarm operating mode is particularly advantageous for identifying patients suffering from PNES, as their subjective assessment of when he or she is having a seizure is likely to be influenced by the generated alarm or warning.

In one embodiment, seizures may be detected using the seizure detection algorithm disclosed in DK 201100556 A and corresponding U.S. patent application publication 2014/0163413, which may be implemented in a body worn device operated in the non-alarm mode. The seizure detection algorithm of DK 201100556 A and corresponding U.S. patent application publication 2014/0163413 is hereby incorporated by reference in this application. The algorithm may count the number of zero-crossings of the sensed signal, when it alternately exceeds the positive and the negative value of a predetermined hysteresis value within a plurality of predetermined time windows. The number of time windows having a count above a first threshold value may then be compared to a second threshold value, if these two values (count and amount of time windows) exceed the two threshold values then a seizure is occurring.

According to one embodiment, the sensor unit measures an electromyographic signal or an acceleration signal, e.g., on at least one limb or skeletal muscle of the patient.

The data may advantageously be measured using an EMG-sensor and/or an accelerometer arranged or coupled to the device. This eliminates the need for attaching multiple EEG-electrodes to the head of the patient and does not require the device to have multiple measuring channels, such as the sixteen channels used in Ipektal et al. The use of at least one EMG-sensor or accelerometer allows the first device to be implemented as a simple and cheap device that allows data to be measured using very few measuring channels, such as one, two, three or four. Two or more sensor units may be arranged in or coupled to the first device, wherein the device may be configured to analyze and evaluate the sensed data in order to determine if a seizure is occurring or not. This allows the device to more accurately detect the seizure onset by measuring two or more different parameters on the patient.

In one embodiment, the data may be measured by an sEMG-sensor with at least two electrodes configured to be placed on a limb muscle or another skeletal muscle of the patient. In one embodiment, the data may be measured by an analogue or digital accelerometer capable of sensing the acceleration in one, two or three directions. The accelerometer may be a capacitive or piezoelectric device. The accelerometer may be placed on a limb muscle or another skeletal muscle of the patient. This allows seizures to be detected by monitoring the movement or muscle activity of the patient's body. The signals are preferably measured where the signals are most prominent thus increasing the measured range of the signals, i.e., the frequency and/or the amplitude. In one embodiment, the sensor unit may be placed on the arm, e.g., the deltoid and/or biceps muscle, or on the chest of the patient.

According to one embodiment, the first device either calculates a root-mean-square value of the sensed signal within at least one time window and compares the RMS-value to the threshold value, or transforms the sensed signal into both the frequency domain and the time domain and compares at least one calculated value from each of the domains to at least one threshold value.

This allows the algorithm to detect the onset of a seizure by applying a predetermined number of time windows, such overlapping time windows, to the sensed signal, and then calculate an RMS-value for each of the time windows. The algorithm may then evaluate the RMS-values and determine if a seizure onset is present or not, e.g., by determining the slope of the RMS-values and comparing it to at least one threshold value. This allows the implemented algorithm to determine whether the measured muscle activity or movements are a GTCS or not.

The algorithm may transform the sensed signal into both the frequency and time domains and extract one or more values, e.g., within a predetermined number of time windows. The algorithm may determine the frequency of the sensed signal and/or the amplitude, such as an RMS-value, of the sensed signal. The values of the time and/or frequency domain may then be compared to at least one threshold value in order to determine whether a seizure onset is present or not. This allows the implemented algorithm to determine whether the measured muscle activity or movements are a GTCS or not.

According to one embodiment, the first device extracts at least one predetermined pattern from the sensed signal, and compares the extracted pattern to the threshold value.

The algorithm may extract one or more patterns from the sensed signal, e.g., the acceleration data, in the time or frequency domain. The extracted pattern may be compared to one or more reference patterns or one or more sets of parameters defining these patterns. In one embodiment, the device may determine the length (time period) of the cloni, i.e., each individual contraction, and/or the length (time period) between each of the cloni. Clinical studies have suggested that the time periods of the cloni in a GTCS are very much alike and of equal length. The studies have suggested that the time periods, i.e., silent periods, increase exponentially for a GTCS. This allows the device to distinguish between a GTCS and a PNES by evaluating the pattern of the measured signal to at least one distinct reference pattern.

According to one embodiment, the measured data from the sensor unit is transmitted directly to a third device and recorded in the third device.

Seizures may be detected by placing at least one set of sensor electrodes, such as electromyography sensor electrodes, on one or more muscles of the patient in predetermined positions. The measured set of data may be transmitted directly to the base unit via a wired connection comprising an optionally plug-and-socket coupling. The measured set of data may instead be transmitted via a wireless communications module in the first device to a mating communications module in the base unit, e.g., as raw data or pre-processed (filtered and/amplified) data. In this embodiment, the third device may be configured to act as an EMG-unit that record the measured/pre-processed data and/or displays the data for further analysis.

The raw or pre-processed data may be continuously measured and recorded in another data file during the time period. This data may be stored in the first device or the base unit, and then transferred or transmitted to the third device for further analysis. This allows the medical staff to evaluate the raw data to confirm that the patient is suffering from PNES, e.g., by analyzing the raw data using another analysis algorithm dedicated for extracting one or more features characteristic of PNES or by using standard evaluation guidelines to determine that the patient is suffering from PNES. This analysis algorithm may differ from the seizure detection algorithm.

According to one embodiment, the patient manually logs the data or at least one subject monitors the patient and manually logs the data.

In one embodiment, seizures may be logged by any subjects monitoring and/or interacting with the patient during the time period. If the patient is placed in his or hers normal environment, then subjects, such as family members, friends and/or colleagues, may log any detected seizures within that time period. If the patient is admitted, then subjects, such as the medical staff, visually monitoring the patient may log any seizures within that time period, e.g., by inputting the data directly into the second device, This allows the patient to be monitored more or less continuously during the time period and allows the number of missing seizures to be reduced.

According to an alternative embodiment, the patient manually logs the data by activating the first device using user input means.

In this configuration, the patient or optionally the subject monitoring the patient is able to manually log each registered seizure by activating user input means located on the first device. The first device, or optionally the base unit, then log at least a time stamp each time the input means is activated. These data are stored in a data file separately from the data file comprising the automatically recorded data and the data file comprising the raw/pre-processed data. The two data files with the lists of time stamps are then transmitted or transferred to the second device for further analysis. This allows the patient/subject to log seizures without having to update a physical list.

As mentioned above, the invention also relates to a system for detecting seizures, such as tonic-clonic seizures, characterized in that:
 the first device is configured to detect at least one seizure within that time period and record at least a second time stamp of that seizure; and
 that the computer unit is configured to compare the recorded data with the logged data and determine if the second time stamps matches the first time stamps or not.

This provides a simple and cheap system for indicating the probability of PNES as well as GTCS which does not require the patient to be admitted to a hospital or a special clinic (e.g., an EMU) and coupled to an EEG system. The first device may be a small battery powered device configured to be placed on the body of the patient by means of a band, a clip or an adhesive layer located on the device. This allows the patient to be situated in his or hers normal environment thus providing a more accurate indication of the factors triggering the seizures. The patient may not act normally, if he or she was admitted thus providing a less accurate indication of the factors triggering the seizures.

In one embodiment, the first device may be configured to a data logger which continuously logs or records data during the time period. The data file may be stored in a memory unit located in the first device or in a third device, such as a base unit. The size and weight of the device may be reduced, if the data is transmitted and stored in the base unit. The recorded data may then be transmitted to the second device, such as a central computer unit, via a wired connection, such as a data cable configured to be removable coupled to at least one of the two devices, or a wireless connection, such as a Bluetooth, WIFI, IR, RF, NFC, ZigBee, or another communications module. The data may instead be transferred to a temporary storage unit, such as a memory stick, which may be coupled to the second device. The connection between the first and third device may be a wired or wireless connection, such as electrical cables, Bluetooth, WIFI, RF, IR, or any other suitable connection.

A physical list or a computer unit, a laptop, a tablet computer, a PDA or a smartphone may be used by the patient or the subject to manually log the time stamp of each seizure. In one embodiment, a data logging device may be configured to record the time stamp when the device is activated, e.g., by the push of a button. The two sets of data may be loaded in the second device which may be configured to electrically compare the data sets, e.g., at least the two lists of time stamps. The second device may be configured to visually indicate or generate an event signal for each recorded or logged seizure and/or any matches or mismatches between the two sets of data. This allows for a quick and simple indication of each registered seizure.

The automatic and manual logging of seizures enables the present system to log seizures only registered by the first device and not the patient/subject, and vice versa. This allows PNES to be distinguished from GTCS by comparing the two lists of time stamps with each other. If no seizures have been recorded by the device and the patient has logged one or more seizures, then the patient may suffer from PNES. If one or more seizures have been recorded by the device and the patient has logged the same seizures, then the patient suffer from epileptic GTCS. If only some of the logged seizures match the recorded seizures, then the patient may suffer from both PNES and epilepsy. This allows PNES to be distinguished from GTCS without the use of video-EEG or index classes. The raw or pre-processed data may be used as back-up or to confirm or disconfirm that the patient is suffering from PNES.

According to one embodiment, the first device is configured to compare the measured parameter to at least one threshold value and determine if a seizure is present or not in a non-alarm mode.

Seizure detection devices are well-suitable to be implemented in the system according to the invention. The device may advantageously comprise an algorithm configured to detect tonic-clonic seizures, such as GTCS, or any seizures having a tonic and/or a clonic phase or any seizures at least having tonic activity. The device may be configured to generate an event signal that may trigger the recording of the data when a seizure onset is detected. Alternatively, the seizure detection algorithm may be implemented in the base unit instead. This allows the device, or the base unit, to record or log any seizures, such as any epileptic seizures, occurring within the time period. The amount of stored and processed data may be reduced by only recording data once a seizure has been detected. This allows the power consumption of the device to be reduced thus increasing the operation time of the device.

In one embodiment, the seizure detection device may be configured to operate in a non-alarm mode. This allows the manual data logging to be uninfluenced by the automatic data logging, thereby ensuring that the patient or subject observing the patient only logs data when he or she believes that a seizure has occurred. This is particularly relevant for patients suffering from PNES. The device is able to detect and record seizures which are not registered by the patient or subject, and vice versa, which in turn increases the reliability of the system.

In one embodiment, the seizure detection algorithm disclosed in DK 201100556 A and corresponding U.S. patent application publication 2014/0163413 may be implemented in a self-adhesive device or a device coupled to a band which is configured to operate in the non-alarm mode. The seizure detection algorithm of DK 201100556 A and corresponding U.S. patent application publication 2014/0163413 is thereby incorporated by reference in this application. The algorithm may be configured to count the number of zero-crossings of the sensed signal, when it alternately exceeds the positive and the negative value of a predetermined hysteresis value within a plurality of predetermined number of time windows. The algorithm may be configured to compare the number of time windows having a count above a first threshold value to a second threshold value. The algorithm may then generate an event signal that may trigger the data recording, if these two values (count and amount of time windows) exceed the two threshold values.

According to one embodiment, the sensor unit is an electromyographic sensor or an accelerometer, and wherein the first device is configured to detect a seizure based on the measured electromyographic signal or the acceleration data.

The first device may advantageously comprise at least one EMG-sensor and/or an accelerometer which eliminates the need for multiple EEG-electrodes and does not require the device to have multiple measuring channels, such as the sixteen channels used in Ipektal et al. article mentioned above. This allows the first device to be implemented as a simple and cheap device that allows data to be measured using very few measuring channels, such as one, two, three or four. Two or more sensor units may be arranged in or coupled to the first device, wherein the device may be configured to analyze and evaluate the sensed data in order to determine whether a seizure is occurring or not. This allows the device to more accurately detect the seizure onset by measuring two or more different parameters on the patient. The second sensor unit may be an EEG-unit, a heart rate sensor, a respiratory sensor, or another suitable sensor unit.

The EMG-sensor unit may be configured as an sEMG-sensor with one or two electrodes configured to be placed on a limb muscle or another skeletal muscle of the patient. The accelerometer may be configured as an analogue or digital accelerometer capable of sensing the acceleration in one, two or three directions. The accelerometer may be a capacitive or piezoelectric device. The accelerometer may be configured to be placed on a limb muscle or another skeletal muscle of the patient. This allows the signal to be measured where the movement or muscle activity is most prominent thus increasing the measured range of the signal, i.e., the frequency and/or the amplitude. In one embodiment, the sensor unit may be placed on the arm, e.g., the deltoid and/or biceps muscle, or on the chest of the patient.

In one embodiment, the algorithm may be configured to apply a predetermined number of time windows, such overlapping time windows, to the sensed signal, and then calculate an RMS-value for each of the time windows. The algorithm may be configured to evaluate the RMS-values and determine if a seizure onset is present, e.g., by determining the slope of the RMS-values and comparing it to at least one threshold value. In one embodiment, the algorithm may be configured to transform the sensed signal into the frequency and/or time domain and extract one or more values, e.g., within a predetermined number of time windows. The algorithm may be configured to determine the frequency and/or amplitude, such as an RMS-value, of the sensed signal. The two values and/or a sum of at least one of these values may be configured to be compared to one or two individual threshold values in order to determine whether a seizure onset is present or not. The device or algorithm may be configured to filter the measured signal by means of a filter function before the parameters are extracted. This allows the implemented algorithm to determine whether the measured muscle activity or movements are a GTCS or not.

In one embodiment, the algorithm may be configured to extract one or more patterns from the sensed signal, e.g., the acceleration data, in the time and/or frequency domain. The algorithm may be configured to compare the extracted pattern to one or more reference patterns or one or more sets of parameters defining these patterns. In one embodiment, the device may be configured to determine the length (time period) of the cloni, i.e., each individual contraction, and/or the length (time period) between each of the cloni. This allows the device to distinguish between a GTCS and a PNES by evaluating the pattern of the measured signal to at least one distinct reference pattern.

According to one embodiment, the first device is configured to transmit the measured data directly to a third device which is configured to record the data.

The device may comprise at least one set of sensor electrodes, such as electromyography sensor electrodes, configured to be placed on one or more muscles of the patient in predetermined positions. The set of sensor electrodes may be coupled directly to the third device via a wired connection comprising an optionally plug-and-socket coupling. The set of sensor electrodes may instead be coupled to a wireless communications module in the first device configured to transmit the measured set of data to a mating communications module in the third device. The first device may be configured to record the data as raw data or comprise means (such as filter means and/or an amplifying means) for pre-processing the data before the transmission. The second device may instead be configured as an EMG-unit configured to record the measured data and/or comprise a display for visually displaying the data.

The first or third device may be configured to record the raw or pre-processed data continuously in a separately data file during the time period. This data may then be transferred or transmitted to the third device for further analysis. The raw data may be evaluated by the medical staff to confirm or disconfirm that the patient is suffering from PNES, e.g., by applying an analysis algorithm dedicated for extracting one or more features characteristic of PNES to the set of data or by using standard evaluation guidelines to determine if the patient is suffering from PNES. The comparator module located in the second device may generate an output signal indicating the probability of the patient suffering from PNES, e.g., a binary value (zero or one) or a value between 0 and 100. The output signal may optionally be transmitted to an evaluation module which generates the indication signal based on the number of mismatches between the two lists of time stamps. The indication signal may also be used to indicate that the patient is not suffering from GTCS, but another type of seizure.

According to one embodiment, the second device comprises user input means for manually logging the data.

The second device may comprise user input means, such as a keyboard, a mouse, or a touch-sensitive display, for manually inputting data into the second device. Subjects, such as the medical staff that visually monitors the patient, may use the user input means to log any seizure with the time period. This allows the patient to be monitored more or less continuously during the time period and allows the number of missing seizures to be reduced.

According to an alternative embodiment, the first device further comprises user input means for manually logging the data.

In this configuration, the first device may be configured to electronically log at least a time stamp every time the input means is activated. The input means may be one or more buttons, touch sensitive areas, or any suitable input means. This allows the patient or subject to manually input data into the device each time a seizure is registered by the patient or the subject monitoring the patient. These data are stored in a data file in the first device or in the base unit separately from the automatically recorded data stored in the first device or the base unit. The two data files are then transmitted or transferred to the second device for further analysis. This allows the patient/subject to log seizures without having to update a physical list.

According to one particular use of the invention, a seizure detection device comprising an electromyographic sensor unit is coupled to a limb or skeletal muscle of a patient to detect an indication of psychogenic non-epileptic seizures.

A portable battery powered device, such as a seizure detection device, comprising one or more EMG-sensor units is particularly suited to be implemented in the above described method and/or system. The EMG-sensor or electrodes thereof may advantageously be placed on a limb muscle or skeletal muscle of the patient. This allows the device to indicate the probability of a PNES by only measuring the muscle activity of that limb.

According to one particular use of the invention, a seizure detection device comprising an accelerometer is coupled to a body of a patient to detect an indication of psychogenic non-epileptic seizures.

A portable battery powered device, such as a seizure detection device, comprising at least one accelerometer is particularly suited to be implemented in the above described method and/or system. The accelerometer may advantageously be placed on a limb muscle or skeletal muscle of the patient. This allows the device to indicate the probability of a PNES by only measuring the movement (acceleration) of that limb.

An embodiment of the invention will now be described by way of an example only and with reference to the accompanying drawings.

DETAILED DESCRIPTION OF THE INVENTION

In the following text, the figures will be described one by one and the different parts and positions seen in the figures will be numbered with the same numbers in the different figures. Not all parts and positions indicated in a specific figure will necessarily be discussed together with that figure.

Figure 1:
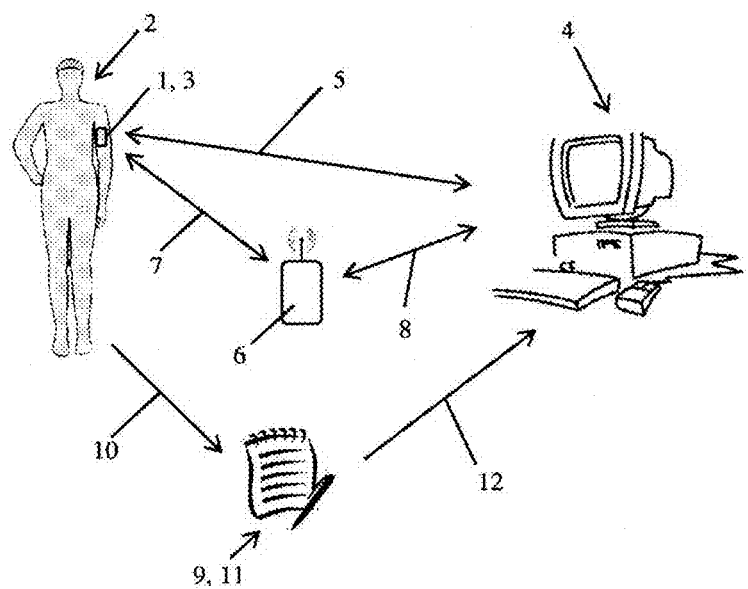
FIG. 1 shows a block diagram of a first exemplary embodiment of the system according to the invention.

FIG. 1 shows a block diagram of a first exemplary embodiment of the system. A portable device 1 may be placed on the body of a patient 2 and held in place by means of a band (not shown) or an adhesive layer on the device 1. The device 1 may be placed on a limb muscle or skeletal muscle of the body, e.g., on an arm of the patient 2.

The device 1 may comprise a removable power source (not shown) in the form of one or more batteries coupled to a power circuit arranged inside the device 1. The power circuit may be configured to power the electrical components located in the device 1.

At least one sensor unit 3 may be arranged in the device 1 and configured to measure at least one parameter on the body of the patient 2. The sensor unit 3 may be configured as an EMG-sensor comprising at least two electrodes configured to measure an electromyographic signal on the body of the patient 2. The measuring electrodes may be positioned on one muscle, such as the deltoid and/or tibial anterior muscle, wherein one of the electrodes may be used as a reference electrode for the other electrode. The sensor unit 3 may instead be configured as an accelerometer configured to measure the acceleration in one, two or three directions.

The device 1 may comprise a microprocessor unit in which a seizure detection algorithm may be implemented for detecting a tonic-clonic seizure, such as a GTCS. The microprocessor unit may be coupled to the sensor unit 3 and may be configured to filter out any noise and other unwanted signals. The algorithm may be configured to extract or calculate one or more parameters from the measured data and compare the extracted or calculated data to at least one threshold value. If the measured data exceeds the threshold values, a seizure is detected and the algorithm may generate an event signal that activates the recording of the data and/or indicates that a seizure is detected.

In one embodiment, the seizure detection algorithm disclosed in DK 201100556 A and corresponding U.S. patent application publication 2014/0163413 may be implemented in the device 1 and configured to operate in a non-alarm mode. The seizure detection algorithm of DK 201100556 A and corresponding U.S. patent application publication 2014/0163413 is thereby incorporated by reference in this application. The algorithm may be configured to count the number of zero-crossings of the sensed signal, when it alternately exceeds the positive and the negative value of a predetermined hysteresis value within a predetermined number of time windows. The algorithm may be configured to compare the number of time windows having a count above a first threshold value to a second threshold value. The algorithm may in the non-alarm mode generate an event signal that may trigger the data recording, e.g., recording the time stamp for each seizure, if these two values exceed the two threshold values. The event signal may not trigger any alarm or warning that alert the patient 2 to the onset of a seizure. The device 1 may be configured to record data over a predetermined time period, e.g., ranging from one hour to seven days.

A second device 4 in the form of a central computer unit may be configured to be coupled to the first device 1, e.g., via a wired or wireless connection 5. The connection 5 may be a data cable or a BLUETOOTH®, RF or WIFI connection. The recorded data may then be transferred from the first device 1 to the second device 2 for further analysis.

In one embodiment, the first device 1 may be configured to be coupled to a third device 6 via another wired or wireless connection 7. The connection 7 may be a wireless BLUETOOTH® or WIFI connection. The third device 6 may be configured as a base unit located within a predetermined distance from the patient 2. The base unit 6 may be configured to be coupled to the second device 4 via yet another wired or wireless connection 8. The connection 8 may be a data cable or a BLUETOOTH®, RF or WIFI connection. The seizure detection algorithm may instead be implemented in the third device 6 so that the first device 1 acts as a simple sensing unit that transmits the measured data to the third device 6 via the connection 7 for storage. The third device 6 may then be configured to detect the seizures in the non-alarm mode.

One of the devices 1, 6 may be configured to continuously record the raw or pre-processed data in a separate data file which may be transmitted or transferred directly to the second device 4 or indirectly via the third device 6.

The system may comprise means 9 for manually logging data, e.g., the time stamp for each seizure, descriptive of a seizure over the time period. The patient may log 10 the time stamp for any detected seizure within the time period on a physical list 9 managed by the patient 2. The list 9 may instead be an electrical list configured to be loaded and executed on a computer unit 11, a laptop, a tablet computer, a PDA or a smartphone. If the data have been logged 10 electronically, the logged data may then be loaded into the second device 4 via a wireless or wired connection 12. The connection 12 may be a data cable or a Bluetooth or WIFI connection. If the data have been logged 10 physically, the logged data may then be inputted into the second device 4 via a keyboard, touch-sensitive display or the like.

The second device 4 may be configured to compare the two sets of data, e.g., the two lists of time stamps, with each other. The second device 4 may be configured to match a time stamp recorded by the first device 1 to a time stamp manually logged by the patient 2. The second device 4 may comprise a display configured to graphically display the two sets of data. The second device 4 may be configured to graphically indicate each recorded and/or logged seizure.

The second device 4 may be configured to graphically indicate any matches and/or mismatches between the recorded time stamps and the logged time stamps. If the first device 1 has not recorded any seizures and the patient 2 has logged one or more seizures, then the patient 2 may suffer from PNES. If the first device 1 has recorded one or more seizures and the patient 2 has logged the same seizures, then the patient 2 may have epilepsy. If the patient 2 has logged more seizures than those recorded by the device 1, where some of the logged seizures correspond to those logged by the device 1, then the patient 2 may suffer from both PNES and epilepsy. This allows the device 4 or the medical staff operating the device 4 to distinguish PNES from GTCS in a simple and cheap manner.

Figure 2:
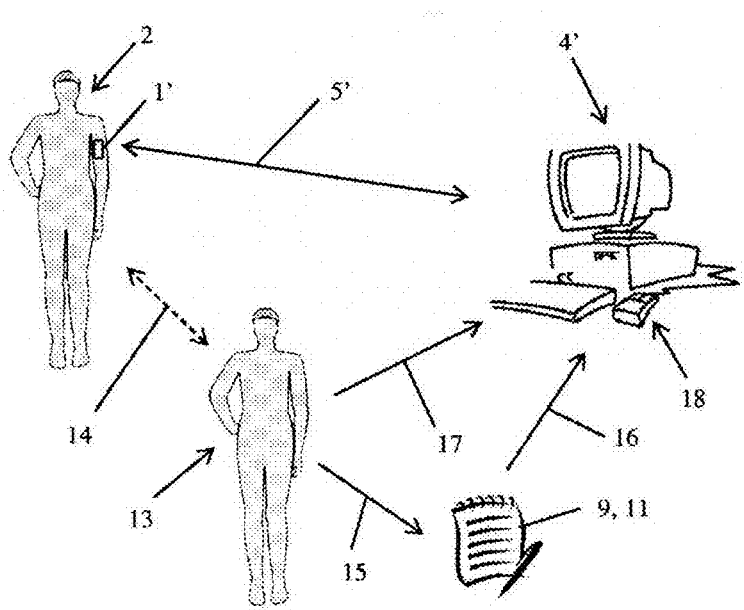
FIG. 2 shows a block diagram of a second exemplary embodiment of the system according to the invention.

FIG. 2 shows a block diagram of a second exemplary embodiment of the system. In this embodiment, the data may be manually logged by any subject 13 that monitors and/or interacts 14 with the patient 2. The patient 2 may be admitted to a hospital or special clinic for observation. The patient 2 may be continuously monitored by the subject 13, e.g., the medical staff, during the admission. The subject 13 may manually log 15 the data, e.g., the time stamp for each seizure, on a physical list 9. The list 9 may instead be an electrical list configured to be loaded and executed on a computer unit 11, a laptop, a tablet computer, a PDA or a smartphone. If the data have been logged 15 electronically, the logged data may then be loaded into the second device 4' via a wireless or wired connection 16. The connection 16 may be a data cable or a BLUETOOTH®, RF or WIFI connection. If the data have been logged 15 physically, the logged data may then be inputted into the second device 4' via a keyboard, touch-sensitive display or the like. The subject 13 may instead log 17 the data directly into the second device 4' using user input means 18 in form a keyboard or a touch-sensitive display.

The first device 1 may be configured as a sensing unit 1' comprising at least one set of sensor electrodes (not shown) configured to be placed on the body of the patient 2. The sensing unit 1' may comprise up to twenty-five sensor electrodes or more. The sensor electrodes may be coupled directly to the second device 4 via a wired connection 5'. The connection 5' may be a data cable comprising an optional plug-and-socket coupling for separating the two devices 1', 4'. The second device 4' may be configured as an electromyographic unit 4' configured to record the measured data from the sensing unit 1'. The second device 4' may comprise a display module configured to display the recorded data from the device 1' and/or the data logged 15, 17 by the subject 13.

The invention is not limited to the embodiments described herein and may be modified or adapted without departing from the scope of the present invention as described in the patent claims below.

What is claimed is:

1. A method of indicating the probability of non-epileptic seizures, wherein the method comprises the steps of:
   automatically recording patient data over a predetermined time period using a portable seizure detection device placed on a patient's body, wherein the portable seizure detection device comprises at least one sensor unit measuring at least one parameter on the patient's body, the portable seizure detection device configured for detection of seizures;
   transmitting the recorded data from the portable seizure detection device to a data processor for further analysis;
   operating the portable seizure detection device in a non-alarm mode in which the at least one parameter is compared to at least one threshold value for determining whether a seizure is present or not, in order to provide non-alarm mode recorded data indicating the presence of any detected seizures;
   receiving manually logged data comprising at least a first time stamp of at least one seizure within the predetermined time period,
   comparing the non-alarm mode recorded data to the manually logged data in the data processor, and
   determining if the non-alarm mode recorded data matches the manually logged data or not in order to determine said probability of non-epileptic seizures.

2. A method according to claim 1, further comprising automatically detecting at least one seizure within the predetermined time period with the portable seizure detection device and recording at least a second time stamp of the at least one seizure detected by the portable seizure detection device, and comparing the second time stamp to the first time stamp to determine if the second time stamp matches the first time stamp or not.

3. A method according to claim 1, wherein the at least one sensor unit measures one of an electromyographic signal and an acceleration signal.

4. A method according to claim 3, wherein said one of an electromyographic signal and an acceleration signal is measured on at least one of a limb and skeletal muscle of the patient.

5. A method according to claim 3, wherein the portable seizure detection device calculates a root-mean-square value of the at least one parameter within at least one time window and compares the root-mean-square-value to the at least one threshold value.

6. A method according to claim 3, wherein the portable seizure detection device transforms the at least one parameter into both a frequency domain and a time domain, and compares at least one calculated value from each of the frequency and time domains to the at least one threshold value.

7. A method according to claim 3, wherein the portable seizure detection device extracts at least one predetermined pattern from the at least one parameter, and compares the at least one pattern to the at least one threshold value.

8. A method according to claim 1, wherein the signal from the at least sensor unit is transmitted directly to base unit recorded in the base unit.

9. A method according to claim 1, wherein the patient manually logs the data or at least one subject monitoring the patient manually logs the data.

10. A system for indicating the probability of non-epileptic seizures, comprising:
 a portable seizure detection device configured to be placed on a patient's body, wherein the portable seizure detection device comprises at least one sensor unit configured to measure at least one parameter on the patient's body, and is configured to automatically record data over a predetermined time period;
 a computer unit configured to be coupled to the portable seizure detection device and comprising a data processor configured to analyze data recorded over said predetermined time period; and
 a data logger configured for manually logging data comprising at least a first time stamp of at least one seizure within the predetermined time period time period, and
 wherein the portable seizure detection device is configured to operate in a non-alarm mode in which the at least one parameter is compared to at least one threshold value for determining whether a seizure is present or not, in order to provide non-alarm recorded data indicating the presence of any detected seizures; and
 wherein the computer unit is configured to compare the non-alarm recorded data with the manually logged data and determine if the recorded data matches the manually logged data or not in order to determine said probability of non-epileptic seizures.

11. A system according to claim 10, wherein the portable seizure detection device is configured to automatically detect at least one seizure within the predetermined time period and to record at least a second time stamp of the at least one seizure, and wherein the computer unit is configured to compare the second time stamp to the first time stamp to determine if the second time stamp matches the first time stamp or not.

12. A system according to claim 8, wherein the at least one sensor unit is one of an electromyographic sensor and an accelerometer, and wherein the portable seizure detection device is configured to detect said seizure based on the signal from the electromyographic sensor or accelerometer.

13. A system according to claim 10, wherein the portable seizure detection device is configured to transmit a signal from the at least one sensor unit directly to a base unit which is configured to record said signal.

14. A system according to claim 10, wherein one of portable seizure detection device and the computer unit comprises a data logger configured for manually logging the data.

* * * * *